(12) United States Patent
Satragno et al.

(10) Patent No.: US 8,761,861 B2
(45) Date of Patent: *Jun. 24, 2014

(54) MAGNETIC RESONANCE IMAGING METHOD INCLUDING COORDINATED ROTATION OF PATIENT TABLE AND MAGNETIC STRUCTURE

(75) Inventors: Luigi Satragno, Genoa (IT); Eugenio Biglieri, Masio (IT); Fabio Rezzonico, Como (IT); Osvaldo Pugliese, Genoa (IT); Orfeo Contrada, Genoa (IT); Trequattrini Alessandro, Genoa (IT)

(73) Assignee: Esaote S.p.A., Genoa (IT)

( * ) Notice: Subject to any disclaimer, the term of this patent is extended or adjusted under 35 U.S.C. 154(b) by 1911 days.

This patent is subject to a terminal disclaimer.

(21) Appl. No.: 12/010,993

(22) Filed: Jan. 31, 2008

(65) Prior Publication Data

US 2008/0161676 A1 Jul. 3, 2008

Related U.S. Application Data

(62) Division of application No. 10/390,175, filed on Mar. 18, 2003, now Pat. No. 8,064,984.

(51) Int. Cl.
*A61B 5/00* (2006.01)

(52) U.S. Cl.
USPC .......................................... 600/415; 324/321

(58) Field of Classification Search
None
See application file for complete search history.

(56) References Cited

U.S. PATENT DOCUMENTS

| | | |
|---|---|---|
| 4,490,675 A | 12/1984 | Knuettel et al. |
| 4,534,076 A | 8/1985 | Barge |
| 4,534,358 A | 8/1985 | Young |
| 4,608,991 A | 9/1986 | Rollwitz |
| 4,613,820 A | 9/1986 | Edelstein et al. |
| 4,629,989 A | 12/1986 | Riehl et al. |
| 4,641,119 A | 2/1987 | Moore |
| 4,644,275 A | 2/1987 | Young |
| 4,651,099 A | 3/1987 | Vinegar et al. |
| 4,668,915 A | 5/1987 | Daubin et al. |
| 4,672,346 A | 6/1987 | Miyamoto et al. |
| 4,679,022 A | 7/1987 | Miyamoto et al. |
| 4,691,163 A | 9/1987 | Blass et al. |
| 4,707,663 A | 11/1987 | Minkoff et al. |
| 4,766,378 A | 8/1988 | Danby et al. |
| 4,777,464 A | 10/1988 | Takabatashi et al. |
| 4,829,252 A | 5/1989 | Kaufman |

(Continued)

FOREIGN PATENT DOCUMENTS

DE 313073 12/1990

*Primary Examiner* — Unsu Jung
*Assistant Examiner* — Amanda Lauritzen Moher
(74) *Attorney, Agent, or Firm* — Buchanan Ingersoll & Rooney PC

(57) ABSTRACT

A magnetic resonance imaging apparatus includes a magnet having a two poles and a wall connecting the poles; the poles delimiting a patient-imaging space; and a table which is slidably connected to one of the two poles between the two poles and which table extends substantially parallel to the two poles; a drive for displacing the table relative to the magnet; a lock for locking the table in a selected position relative to the magnet; a drive for rotating the magnet about the axis; the table connected to the magnet such that the table rotates with the magnet when the magnet rotates about the axis; the magnet and the table being rotatable from a position in which the poles and the table are horizontal to a position in which the table and the poles are vertical.

10 Claims, 7 Drawing Sheets

(56) References Cited

U.S. PATENT DOCUMENTS

| | | | |
|---|---|---|---|
| 4,875,485 | A | 10/1989 | Matsutani |
| 4,892,252 | A | 1/1990 | Bruninga |
| 4,908,844 | A | 3/1990 | Hasegawa |
| 4,924,198 | A | 5/1990 | Laskaris |
| 4,943,774 | A | 7/1990 | Breneman et al. |
| 4,968,937 | A | 11/1990 | Akgun |
| 4,985,678 | A | 1/1991 | Gangarosa et al. |
| 4,989,608 | A | 2/1991 | Ratner |
| 5,008,624 | A | 4/1991 | Yoshida |
| 5,061,897 | A | 10/1991 | Danby et al. |
| 5,065,761 | A | 11/1991 | Pell |
| 5,124,651 | A | 6/1992 | Danby et al. |
| 5,134,374 | A | 7/1992 | Breneman et al. |
| 5,153,546 | A * | 10/1992 | Laskaris ............ 335/216 |
| 5,155,758 | A | 10/1992 | Vogl |
| 5,162,768 | A | 11/1992 | McDougall et al. |
| 5,194,810 | A | 3/1993 | Breneman et al. |
| 5,197,474 | A | 3/1993 | Englund et al. |
| 5,207,224 | A | 5/1993 | Dickinson et al. |
| 5,211,165 | A | 5/1993 | Dumoulin et al. |
| 5,229,723 | A | 7/1993 | Sakurai et al. |
| 5,250,901 | A | 10/1993 | Kaufman et al. |
| 5,290,266 | A | 3/1994 | Rohling et al. |
| 5,291,890 | A | 3/1994 | Cline et al. |
| 5,304,932 | A | 4/1994 | Carlson |
| 5,305,365 | A | 4/1994 | Coe |
| 5,305,749 | A | 4/1994 | Li et al. |
| 5,315,276 | A | 5/1994 | Huson et al. |
| 5,349,956 | A | 9/1994 | Bonutti |
| 5,382,904 | A | 1/1995 | Pissanetzky |
| 5,382,905 | A | 1/1995 | Miyata et al. |
| 5,386,447 | A | 1/1995 | Siczek |
| 5,412,363 | A | 5/1995 | Breneman et al. |
| 5,423,315 | A | 6/1995 | Margosian et al. |
| 5,436,607 | A | 7/1995 | Chari et al. |
| 5,475,885 | A | 12/1995 | Ishikawa |
| 5,486,700 | A | 1/1996 | Silberklang et al. |
| 5,490,513 | A | 2/1996 | Damadian et al. |
| 5,519,372 | A | 5/1996 | Palkovich et al. |
| 5,565,834 | A | 10/1996 | Hanley et al. |
| 5,592,090 | A | 1/1997 | Pissanetzky |
| 5,606,970 | A | 3/1997 | Damadian |
| 5,623,241 | A | 4/1997 | Minkoff |
| 5,640,958 | A | 6/1997 | Bonutti |
| 5,666,056 | A | 9/1997 | Cuppen |
| 5,689,190 | A | 11/1997 | Cuppen |
| 5,735,278 | A | 4/1998 | Hoult et al. |
| 5,743,264 | A | 4/1998 | Bonutti |
| 5,754,085 | A | 5/1998 | Danby et al. |
| 5,779,637 | A | 7/1998 | Palkovich et al. |
| 5,874,880 | A * | 2/1999 | Laskaris et al. ............ 335/216 |
| 5,983,424 | A | 11/1999 | Naslund |
| 6,011,396 | A | 1/2000 | Eckels et al. |
| 6,023,165 | A | 2/2000 | Damadian et al. |
| 6,201,394 | B1 | 3/2001 | Danby et al. |
| 6,215,308 | B1 | 4/2001 | Takekoshi et al. |
| 6,246,239 | B1 | 6/2001 | Krogmann et al. |
| 6,385,481 | B2 | 5/2002 | Nose et al. |
| 6,411,088 | B1 | 6/2002 | Kuth et al. |
| 6,414,490 | B1 * | 7/2002 | Damadian et al. ............ 324/319 |
| 6,424,854 | B2 | 7/2002 | Hayashi et al. |
| 6,504,371 | B1 | 1/2003 | Damadian et al. |
| 8,064,984 | B2 * | 11/2011 | Satragno et al. ............ 600/415 |
| 2013/0144158 | A1 * | 6/2013 | Satragno et al. ............ 600/415 |

\* cited by examiner

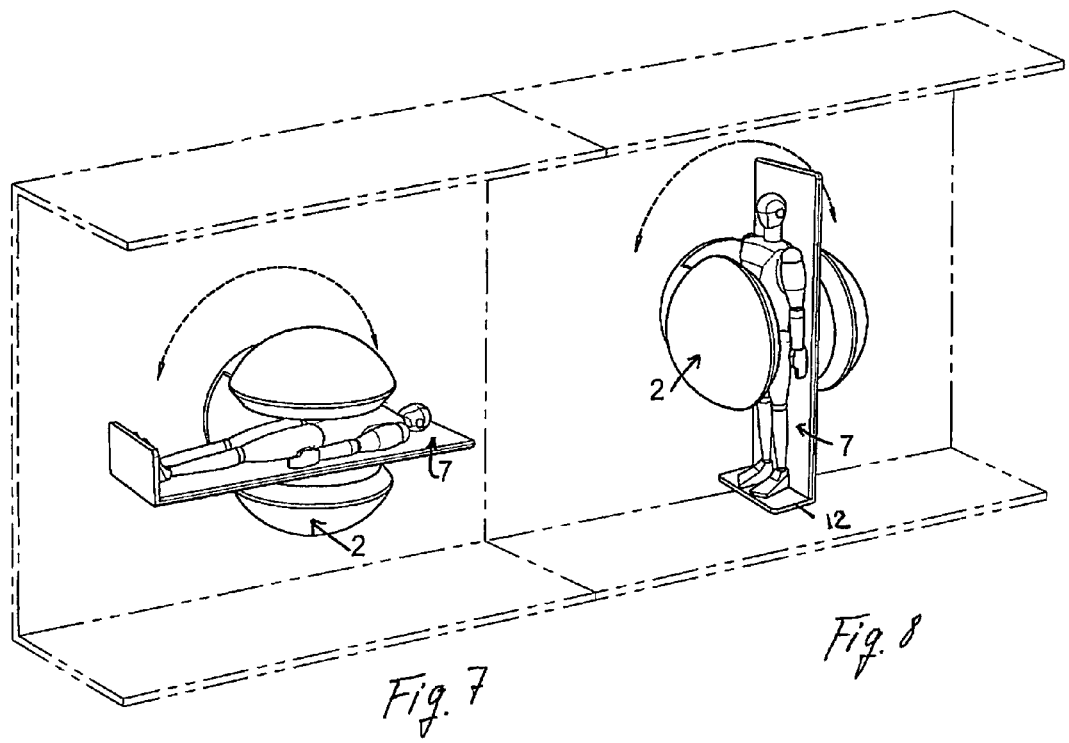
Fig. 7
Fig. 8
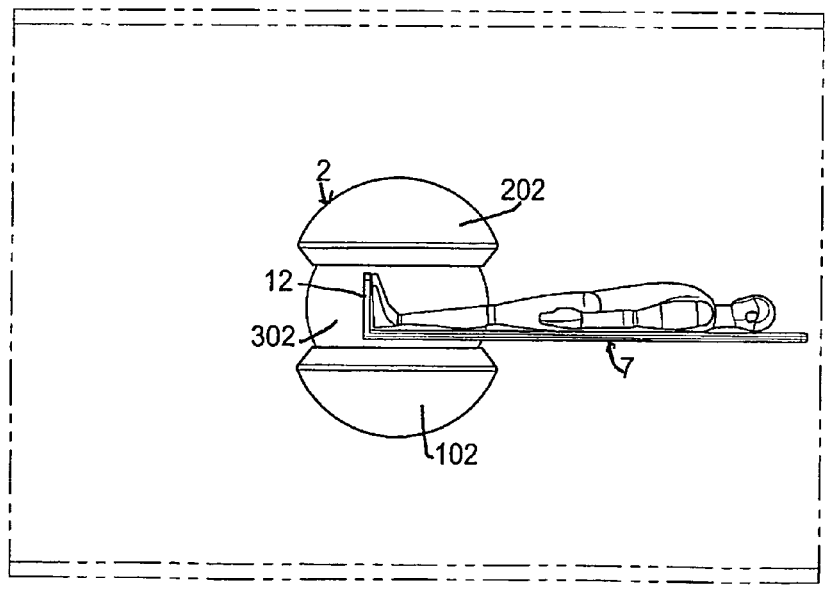
Fig. 3

MAGNETIC RESONANCE IMAGING METHOD INCLUDING COORDINATED ROTATION OF PATIENT TABLE AND MAGNETIC STRUCTURE

BACKGROUND OF THE APPLICATION

1. Field of the Invention

The invention relates to a magnetic resonance imaging apparatus, and particularly to a multipurpose dedicated imaging apparatus having improved features for imaging the region of the vertebral column.

2. Description of the Related Art

Imaging the vertebral column may require the possibility of bringing the patient in an upright position in order to have the vertebral column loaded by the weight of the patient. In the normal laying down position of the patient on a bed or table having an horizontal orientation, the vertebral column will be in an unloaded and ideal condition. Thus, most pathologies may not arise clearly and the examination will lead to unclear results or to negative results despite the fact that the patient is showing typical symptoms of a disease of the vertebral column.

Actually known magnetic resonance imaging apparati use so called total body scanners which magnetic structure houses the entire body or a considerable part of it inside the patient examining space defined by the magnetic structure.

U.S. Pat. Nos. 6,414,490 and 6,504,371 disclose magnetic resonance imaging apparatus of the above mentioned kind. The magnetic structure is designed to generate a horizontal magnetic field. The patient is brought inside the examining space by means of a patient positioning device which is a bed or table mounted on a carriage, which bed or table can be further tilted around horizontal axis for giving different orientations to the bed or table with respect to the vertical direction. Furthermore, in order to focus the region of the patient to be imaged, the bed or table or carriage may be associated with an elevator which displaces the patient up and down relative to the examining space between the poles of the magnetic structure.

The actual devices are very big, heavy, and expensive. Big and heavy magnetic structures have problems of installation, since the room where the imaging apparatus has to be installed must necessarily have a floor which can support the weight of the imaging apparatus. Furthermore, the room must be sufficiently big to permit installation.

The patient positioning device is also relatively expensive due to the tiltable or swingable bed or table and due to the necessity of an elevator for displacing the patient relative to the imaging space in the magnetic structure.

On the other hand, even if the anatomic region of the vertebral column is a very large one, usually examination through imaging is carried out for only a certain specific part of the vertebral column.

OBJECTS AND SUMMARY

An object of the present invention is to provide for a magnetic resonance imaging apparatus which has a smaller magnetic structure than the conventional so called total body apparatus and which allows nevertheless imaging of the vertebral column under various conditions.

A further aim is to provide for such a magnetic imaging apparatus which has simpler and less expensive means for positioning the patient in the examination space of the magnetic structure.

A further object of the present invention is to provide for a magnetic resonance imaging apparatus which can be used also for examinations of other anatomic regions of the body of the patient, by allowing in a simple way to displace the patient relative to the examination space in the magnetic structure in order to bring the desired anatomic region or a certain limited region thereof in the examination space.

One embodiment of the present invention includes a magnetic resonance imaging apparatus comprising a magnet having a two opposite and spaced apart poles and a column or wall transverse to the poles and connecting the poles; the poles defining two opposite walls delimiting a patient-imaging space, the two opposite walls extending along substantially parallel planes which are substantially perpendicular to a vertical plane; and a patient positioning table which is slidably connected to one of the two poles in a position between the two poles and which table extends substantially parallel to the two opposite poles; the table being slidable with respect to the magnet in a direction parallel to a longitudinal axis of the table; a drive for displacing the table relative to the magnet; a lock for locking the table in a selected position relative to the magnet; the magnet being supported rotatably along a central horizontal axis of the transverse wall or column; a drive provided for rotating the magnet about the axis; the table being connected to the magnet such that the table rotates with the magnet when the magnet rotates about the axis; the magnet and the table being rotatable from a position in which the poles and the table are substantially horizontal to a position in which the table and the poles are substantially vertical, and vice versa; and the rotation of the table and the magnet are locked together by the lock.

Another embodiment of the present invention includes a method for magnetic resonance imaging with a magnetic structure having two opposite poles spaced apart one from the other and oriented substantially perpendicular to a vertical plane and defining a patient imaging space; and a table for a patient secured to one of the two poles in a slidable way in a longitudinal direction of the table relative to the magnetic structure and between the two poles of the magnetic structure, the table being oriented parallel to the poles, the table having a footrest at one end thereof, the magnetic structure and the table being rotatable together around an axis which is transverse to a longitudinal axis of the table and parallel to the table. The method comprises:

rotating the magnetic structure with the table to a patient positioning position in which the table is substantially horizontal;

sliding the table to an end position, in which a part of the table is outside the magnetic structure;

arranging the patient on the table in a lying down position;

sliding the table along its longitudinal axis relative to the magnetic structure until the magnetic structure is correctly centered with a part of the patient's body to be examined;

locking the table relative to the magnetic structure together with the table in a position in which the table is not horizontal or vertical;

carrying out an imaging procedure;

rotating the magnetic structure together with the table to a position in which the table is substantially horizontal; and sliding the table to one of two positions in which a part of the table is outside the magnetic structure and letting the patient step down from the table.

Another embodiment of the present invention includes a method for carrying out magnetic resonance imaging with providing a magnetic structure having two opposite poles spaced apart one from the other and oriented substantially perpendicular to a vertical plane and defining a patient imaging space; and a table having a footrest at one end and slides for engaging guides for a longitudinal displacement of the table; and a table supporting structure which has wheels and which is completely independent from the magnetic structure, one of the poles of the magnetic structure and the table supporting frame have identical guides with which the slides of the table are adapted to engage. The method comprises:

rotating the magnetic structure such that the guides for the table are horizontal and aligning the table supporting frame with the guides of the table supporting frame aligned with the guides on the pole of the magnetic structure; lying the patient down on the table;

sliding the table along a longitudinal direction thereof away from the table supporting frame and against the pole having the guides and engaging at the same time a free end of the slides of the table with the guides on the pole;

sliding the table with the patient on the table until the table is completely disengaged from the table supporting frame and engaged with the pole of the magnetic structure;

sliding further the table along its longitudinal axis relative to the magnetic structure until the magnetic structure is correctly centered with a part of the patient's body to be examined;

supporting the magnetic structure and the table in such a way as to be rotatable together around an axis which is transverse to the longitudinal axis of the table and substantially parallel to the table;

locking the table relative to further sliding and rotating the magnetic structure together with the table with the patient on it in a position in which the table is not horizontal;

carrying out the imaging procedure;

rotating the magnetic structure together with the table back to a position in which the table is substantially horizontal;

sliding the table away from the pole of the magnetic structure onto the table supporting frame.

Another embodiment of the present invention includes a method for carrying out magnetic resonance imaging with a magnetic structure having two opposite poles spaced apart one from the other and oriented substantially perpendicular to a vertical plane and defining a patient imaging space; and a table for a patient to one of the two poles in a slidable way in a longitudinal direction of the table relative to the magnetic structure and between the two poles of the magnetic structure, the table being oriented substantially parallel to the poles; the magnetic structure and the table being rotatable together around an axis which is transverse to the longitudinal axis of the table and parallel to the table. The method comprises:

rotating the magnetic structure together with the table in a position in which the table is not horizontal;

providing a seat plate secured at an angle to the table;

sitting the patient down on the seat plate;

carrying out the imaging procedure; and letting the patient step out of the magnetic structure.

BRIEF DESCRIPTION OF THE DRAWINGS

The magnetic resonance imaging apparatus and the advantages thereof will appear more clearly from the following description made with reference to an embodiment which is illustrated in the annexed drawings which drawings illustrate:

FIGS. 3 to 6 are simplified frontal views of an embodiment of the apparatus according to the invention in its position with the table oriented along the horizontal plane and in different relative positions of the table with respect to the magnetic structure.

FIGS. 7 and 8 are perspective views of an embodiment of the apparatus according to the present invention with the magnetic structure and the table in the position in which the table is horizontal and in the position in which the table is vertical.

DETAILED DESCRIPTION OF THE PREFERRED EMBODIMENTS

Figure 1:
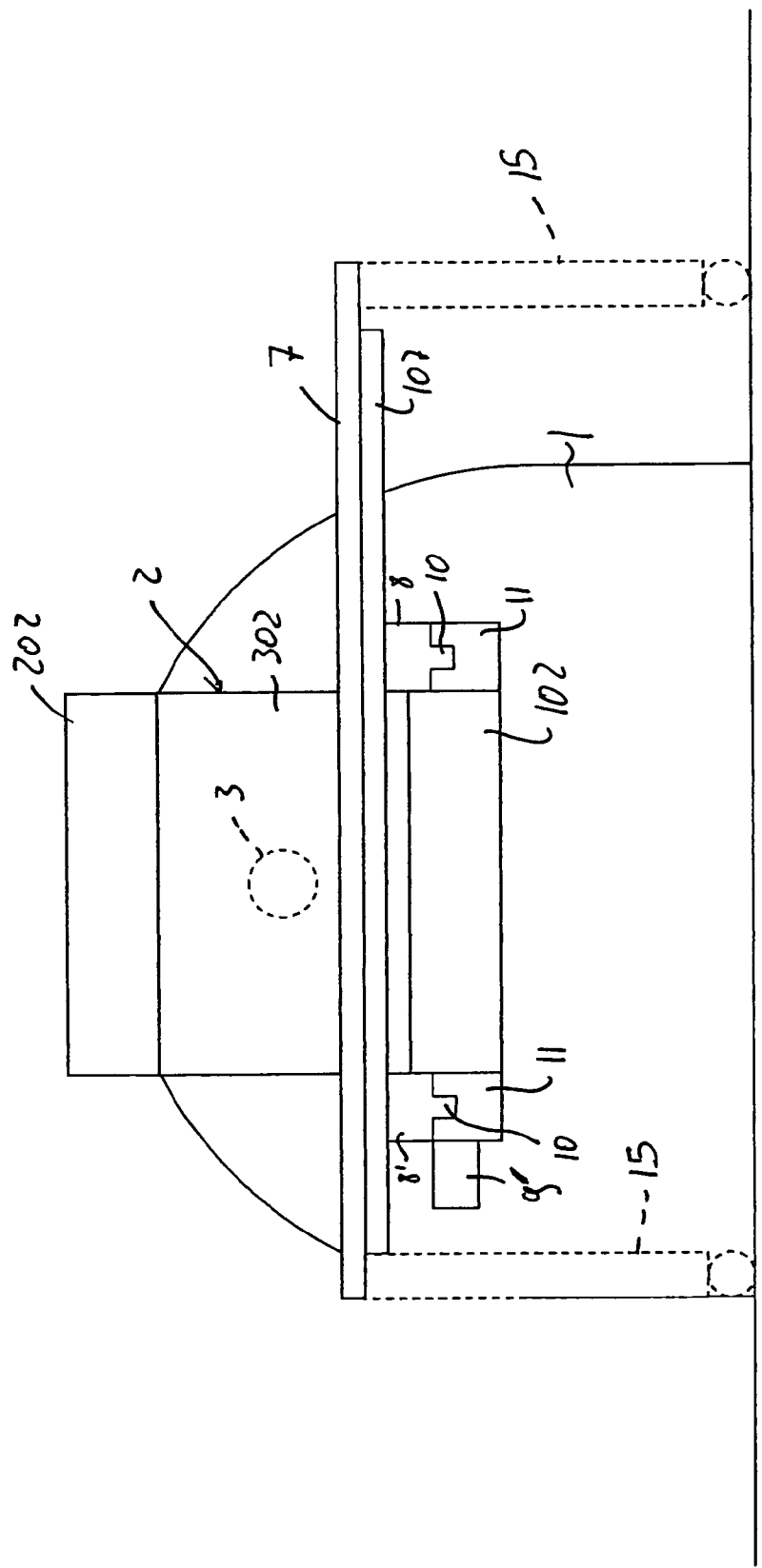
FIG. 1 is a schematic frontal view of an embodiment of a magnetic resonance imaging apparatus according to the invention.
Figure 2:
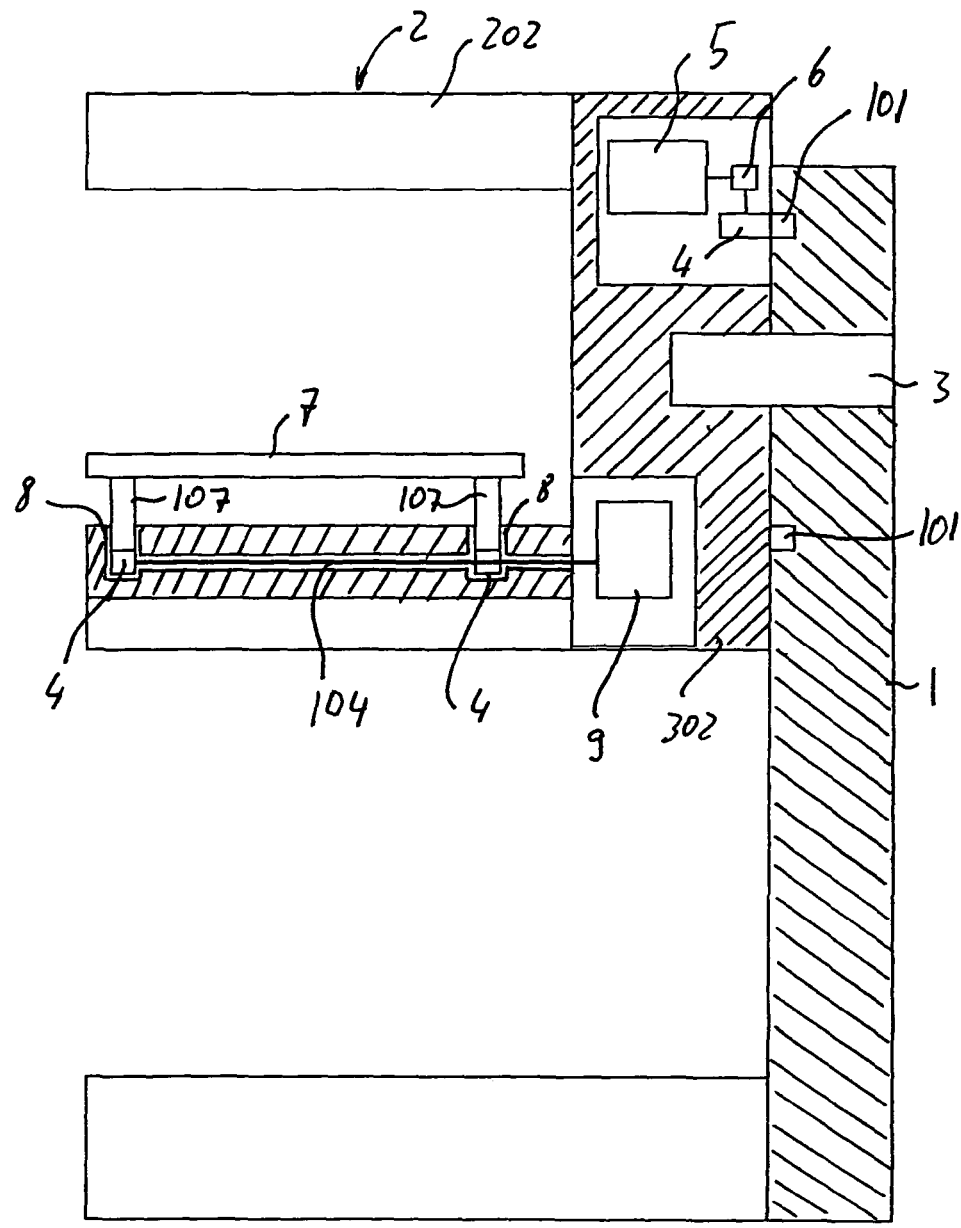
FIG. 2 is a schematic lateral view partly sectioned of the apparatus according to FIG. 1.

Referring now to the Figures, particularly FIGS. 1 and 2, a magnetic resonance imaging apparatus according to an embodiment of the invention is schematically illustrated.

The magnetic resonance imaging apparatus comprises a supporting element 1 in the form of a vertical wall. A magnetic structure 2 is secured to the supporting element 1 in a overhanging way. The magnetic structure 2 comprises two opposite poles 102, 202 which are oriented perpendicularly with respect to the supporting wall 1, and which are connected together in a spaced apart relationship by means of a column or wall 302 which extends parallel to the supporting wall 1 and which is secured to the wall by means of a shaft 3 perpendicular to the supporting wall 1 and to the transverse connecting wall 302 of the magnetic structure 2. The axis of the shaft 3 which is rotatable in a housing in the supporting wall and is also parallel to the poles 102, 202 and perpendicular to the magnetic field generated between them. The axis of the shaft 3 is coincident with the center of symmetry of the wall 302 of the magnetic structure, although this is not a necessary feature in order to ensure the functions of the present magnetic resonance imaging apparatus.

A coaxial frontally toothed crown 101 on the supporting wall 1 cooperates with a driving pinion 4 which is driven by a motor 5 by means of a transmission 6. Thus, the motor 5 can cause the rotation of the magnetic structure 2 around the axis of the shaft 3 relative to the supporting wall 1. Although the frontally toothed coaxial crown 101 is illustrated mounted on the supporting wall 1, the same result could be reached by providing the toothed crown on the wall 302 of the magnetic structure and the motor 5, the transmission 6 and the pinion 4 on the supporting wall. This solution would avoid elements on the wall 302 which could cause disturbance to the circulation of the magnetic flux within said wall 302.

A table 7 is slidably mounted in a direction parallel to its longitudinal axis on the lower pole 102 of the magnetic structure. As used herein, the term "table" may be a bed, bed plate, table plate, or other flat surface on which a patient may lie for purposes of examination. The table or bed plate 7 is oriented with its longitudinal axis perpendicular to the axis of the shaft 3 and parallel to the wall 302 of the magnetic structure 2.

The table 7 is supported slidably in its longitudinal direction by means of a combination of guides and slides, motorized means being also provided for deriving the displacement of the said table 7 relative to the magnetic structure 2.

In the present embodiment, two longitudinal slides 107 are provided underneath the table 7 and are secured thereto. The slides 107 extend along opposite longitudinal sides of the table 7 are slidably engaged in guides 8, 8' provided at the transverse ends of the lower pole 102 of the magnetic structure.

A combination of a longitudinal rack secured to the table 7 and a pinion driven by a motor ensures a motorised displacement of the table along it longitudinal axis and in both directions.

As illustrated, the racks may be formed also by the one or both slides 107, a surface of which has a toothed longitudinal region which engages with a corresponding pinion 4 housed in a recess of the one or both guides 8, 8'. The pinion or pinions 4 are driven by a motor 9 through a shaft 104. See FIGS. 2 and 11.

Figure 11:
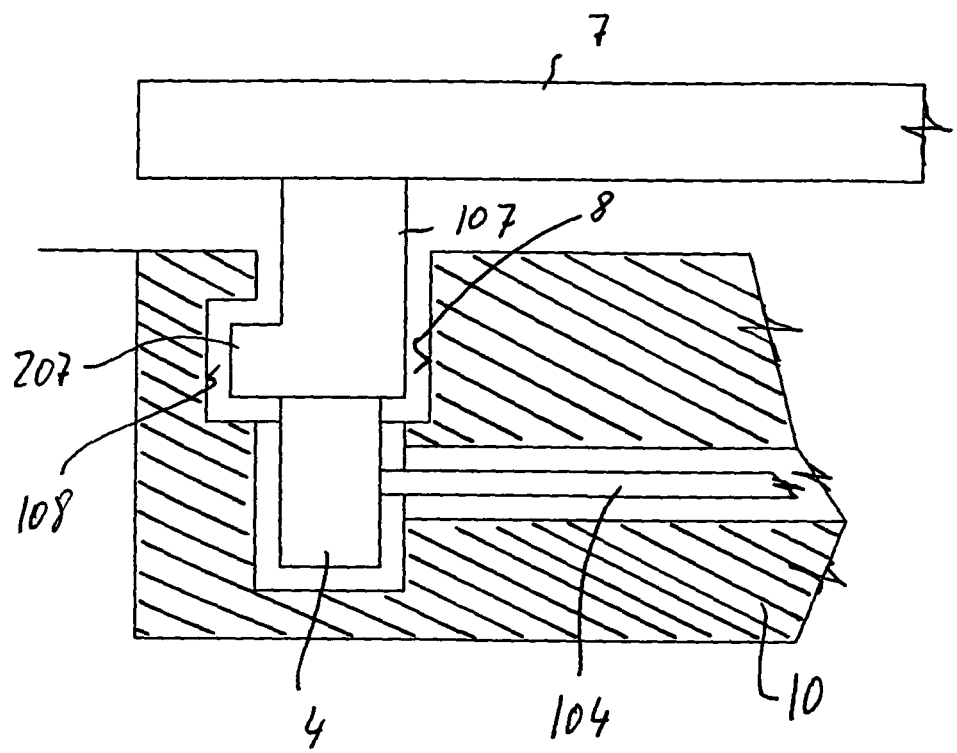
FIG. 11 shows a partial section of a enlarged particular of one slide and guide of the table according to one embodiment of the present invention.

As shown in FIG. 11, the slides 107 and the guides 8, 8' have a cross section which forms a mutual undercut for avoiding the slipping out of the slides 107 from the guides when the magnetic structure is rotated together with the table 7 from the horizontal position of the table to a vertical position.

Many different designs of the slides and of the guides may be chosen. One simple solution illustrated in FIG. 11 comprises a lateral continuous tooth 207 on each slide 107 which engages a lateral continuous slot 108 in the corresponding lateral wall.

Furthermore, nonillustrated releasable locking means of the table 7 relative to the magnetic structure 2 are provided. This locking means may consist in the combination of the rack and pinion mechanism which might be of the nonreversible kind if the motor is deenergised. Alternatively, mechanical locking means, such as releasable locking teeth engaging the rack, may be provided which means may be driven alternatively in an active position of engagement and in an inactive position of disengagement by means of manual, electric or other kinds of actuators.

According to a further feature, the table 7 may be also slidable in a direction transverse to its longitudinal axis, i.e., in a direction perpendicular to the wall 302 of the magnetic structure 2. This may be obtained in a similar way as the method described with reference to the longitudinal displacement of the table 7.

According to the illustrated example, the guides 8, 8' on each side of the pole 102 are arranged on a transverse slide 10 which engages a transverse guide 11. The transverse guide and slides may have a cross-section with mutually engaging undercuts as described with reference to the longitudinal guides and slides and according to FIG. 11. The displacement in the transverse directions may be driven by a motor 9' by means of a combination of racks and pinions as described in detail with reference to the longitudinal guides and slides.

Also for the transverse displacement of the table 7 releasable locking means may be provided which may be activated or deactivated as described with reference to the releasable locking means for the longitudinal displacement of the table 7.

Thanks to the above disclosed construction, the magnetic resonance imaging apparatus according to the present invention allows positioning of the patient on the table 7 when the magnetic structure with the table are rotated in an horizontal position of the poles 102, 202 and of the table 7.

Figure 4:
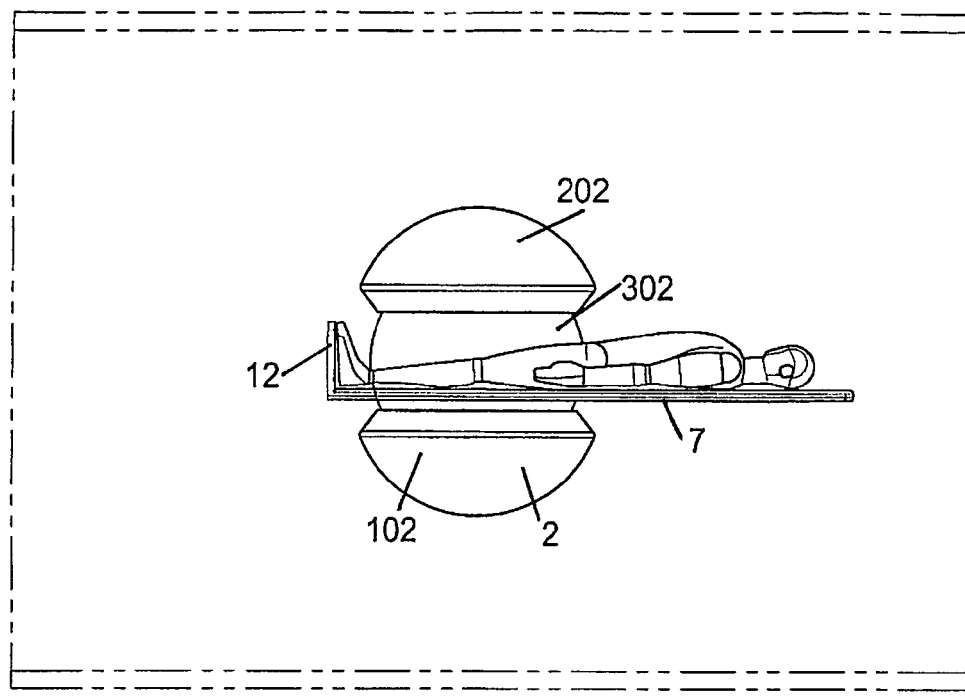
Figure 5:
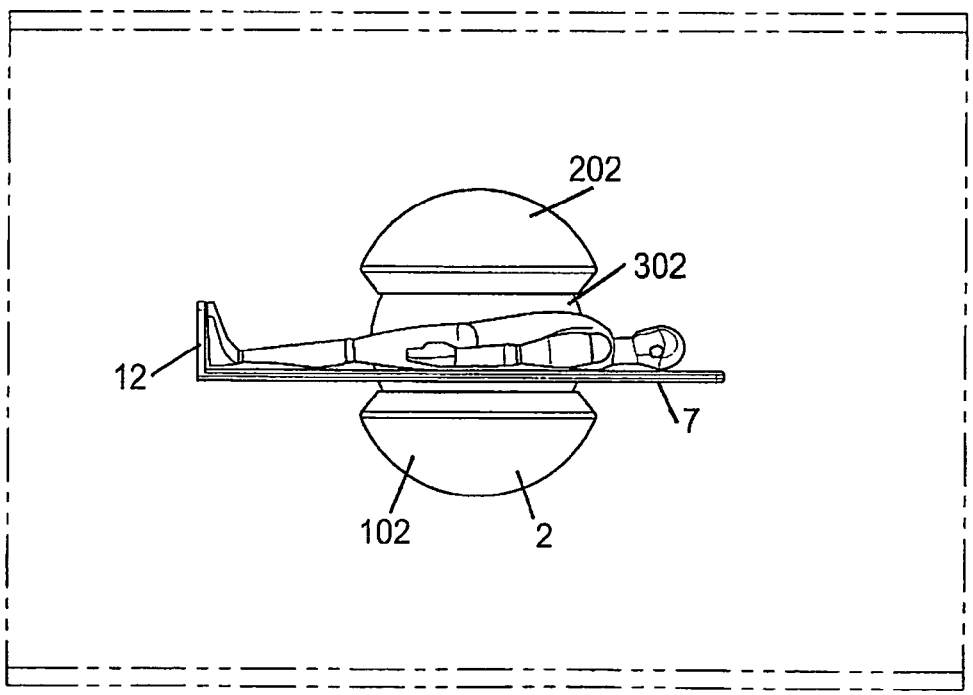
Figure 6:
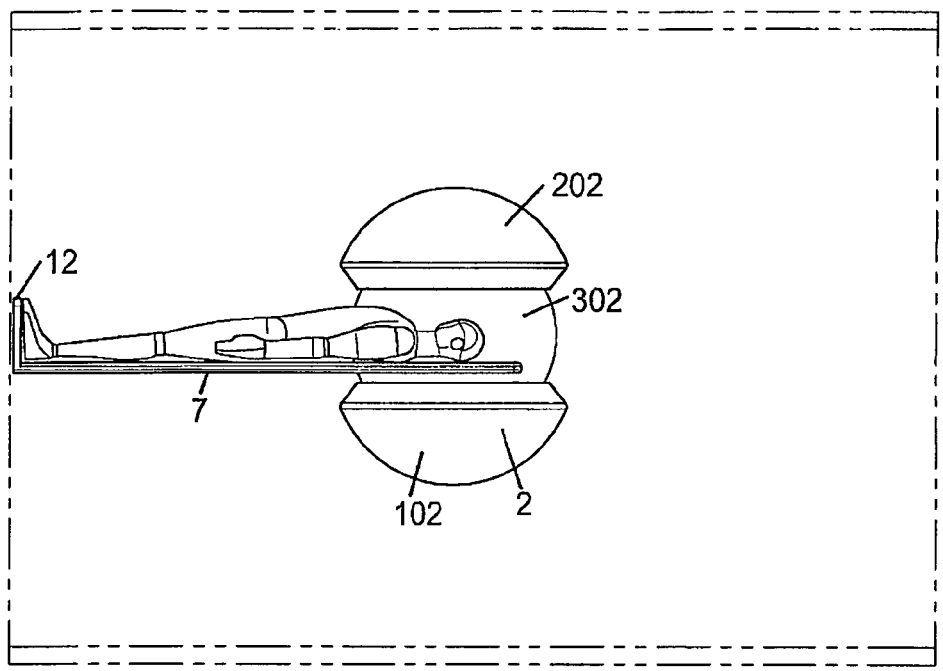

In order for the patient to lie on the table 7, the table 7 may be brought to its maximum longitudinal displacement, as illustrated in FIG. 3. After the patient has taken place correctly on the table, the table may be displaced relative to the magnetic structure 2 in its longitudinal direction or if provided also in its transverse direction. FIGS. 4 to 6 illustrates different relative positions of the table 7 with respect to the magnetic structure 2.

The FIGS. 3 to 6 also clearly illustrate that the magnetic resonance imaging apparatus according to the present invention allows not only to carry out useful images of the vertebral column but due to the fact that the table 7 might be displaced continuously in longitudinal and transverse directions, the patient can be brought every time with a different anatomic region in the examination space formed between the two poles 102, 202, thus allowing different kinds of examinations.

In order to reduce the load on the guides and slides of the overhanging table 7 at its extreme positions (FIGS. 3 and 6), the table might be provided at one or both of its ends with a couple of wheeled legs 15 as is shown in FIG. 1. This allows an extraction of the table from the magnetic structure for almost its entire length, provided the end without the wheeled supporting legs will rest engaged for a terminal length with the magnetic structure.

Once the patient is on the table 7, the magnetic structure 2 can be rotated together with the table 7 through an angle of 90°. In this position the table is vertical and the patient is in an upright position. In order to allow the patient to reach the upright position, at the end of the table associated with the feet a footrest 12 is provided. This footrest may be fixed or it may be formed by a plate which is secured in position to the table after having positioned the patient or the footrest may be formed by a prolongation of the table 7 which is hinged to the table 7 in such a way as to be brought and blocked alternatively in the overhanging position and in a position parallel to the rest of the plate 7.

As is clear from the FIGS. 7 and 8, the magnetic structure and the table may be rotated for an angle less than 90°, thus modulating the load on the vertebral column of the patient due to the weight of the patient itself.

Once imaging has been carried out, the magnetic structure 2 and the table 7 can be rotated again in the position where the table 7 is horizontal. The table can then be displaced to one of its end positions, and the patient can leave the apparatus.

Figure 10:
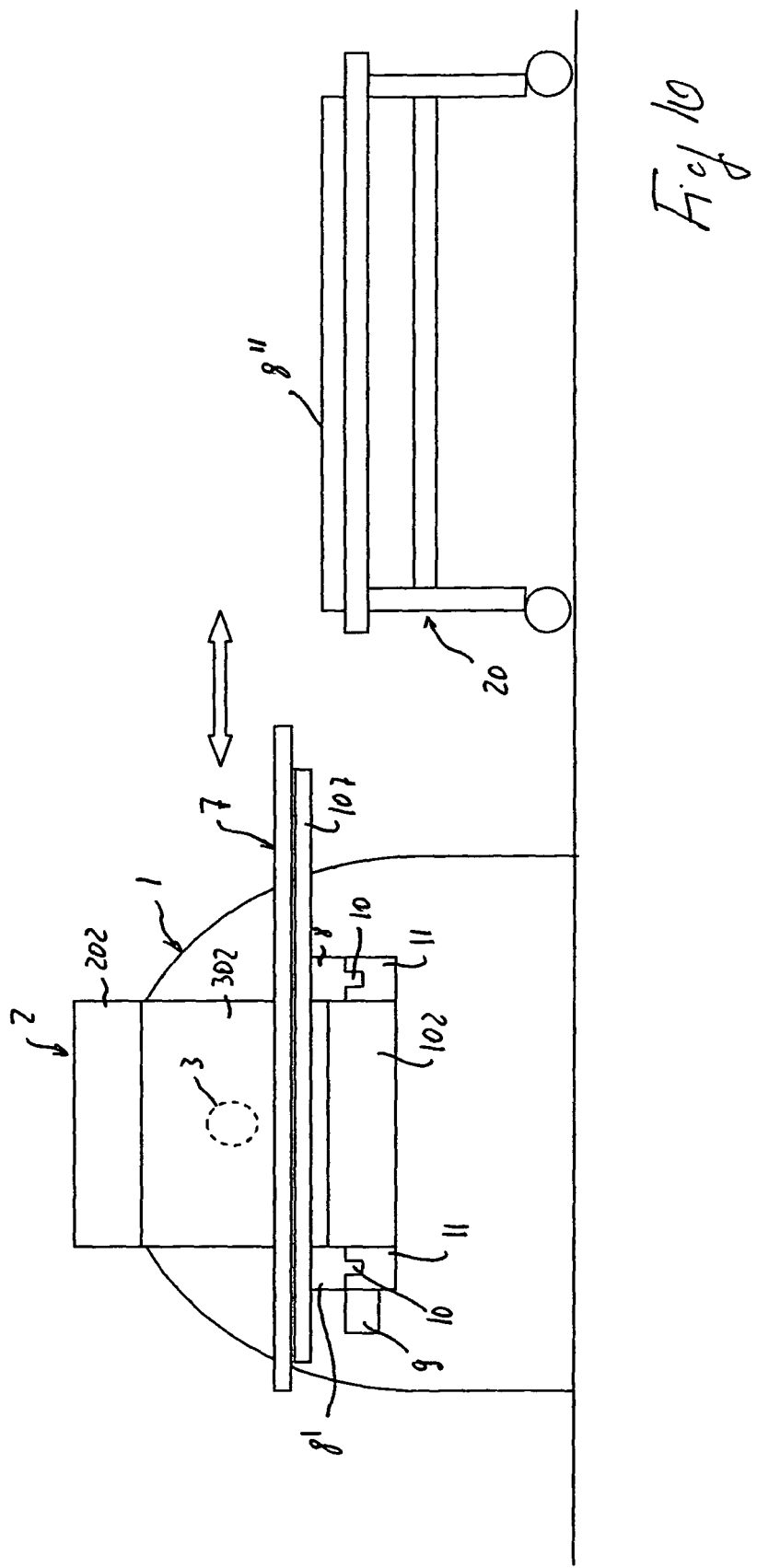
FIG. 10 illustrates a frontal view of an embodiment of the magnetic resonance imaging apparatus according to the present invention in combination with a separate supporting frame for the table.

According to a further improvement illustrated in FIG. 10, a separate supporting structure 20 may be provided for the table 7. This separate supporting structure is formed by a frame having wheeled legs. The supporting structure 20 is provided on its top with guides 8" which are identical in position and cross section to the guides 8,8' for the longitudinal slides 107 of the plate 7. Thus by aligning the guides 8" on the separate supporting structure 20 for the plate 7 with the guides 8, 8' of the pole 102, the table 7 may be transferred by longitudinal displacement from the said supporting structure 20 to the guides 8, 8' on the pole 102, and vice versa. Thus, the patient might be prepared for examination on a table outside the magnetic structure while another patient is subjected to examination in the apparatus.

Because the plate 7 can be inserted in the magnetic structure from one side and extracted from the magnetic structure on the opposite side, and by providing at least two plates 7 with at least two supporting frames 20 one for each plate, it is possible to control the traffic of patients to be examined.

In such a case, the table with a patient who has just finished the examination is extracted from the magnetic structure, for example, from the left hand end of the structure 2 of FIG. 10, while the table 7 with a following patient is inserted in the magnetic structure from the right hand side of the magnetic structure 2.

This solution also allows preparation of the patient for examination on a table outside the magnetic imaging apparatus so that a patient can be prepared for examination while another patient is examined in the apparatus. Providing a disengagement of the bed or table from the magnetic structure from one side of the magnetic structure and the engagement of the following bed or table with the magnetic structure on the opposite side of it the apparatus is even more rational regarding the traffic of patient.

By providing the supporting structure of the table 7 with guides oriented perpendicularly to the longitudinal axis of the table 7 itself, the insertion or extraction of the table 7 in and from the magnetic structure 2 can also be carried out in a transverse direction of the table 7.

Figure 9:
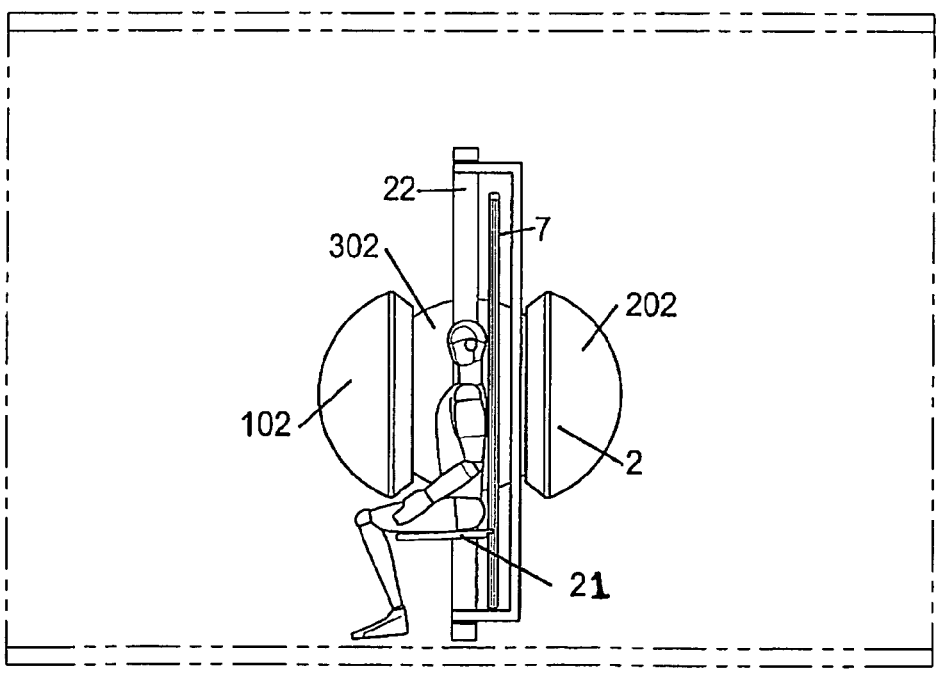
FIG. 9 illustrates a lateral view of an embodiment of the apparatus according to the present invention in which a seat is associated to the table.

According to a further feature which is shown in FIG. 9, a seat plate 21 may be provided. The seat plate 21 may be secured directly to the table 7 at different heights or there might be provided a supporting rod 22 which is secured parallel to the plate 7 to the plate itself or to the magnetic structure. The rod 22 carries an overhanging seat plate, the seat plate being secured to the rod by means of a slide engaging the rod, releasable locking means being provided for locking the seat plate 21 at a desired height.

Thanks to the above embodiments of the magnetic resonance imaging device according to the invention, a method for carrying out the examination particularly of the vertebral column of a patient can be defined. An advantage of this method lies in the fact that a simple and not overdimensioned magnetic structure and patient supporting unit is needed.

The magnetic structure of the imaging apparatus is preferably of the so called dedicated kind, forming a patient imaging space which is at least shorter than the mean height of adult patients. Such magnetic structures are relatively light and less costly than total body magnets or similar magnets. Furthermore such dedicated magnetic structures are handy and can be supported in a displaceable manner without taking into account high expenses for the means which allow the displacement of the magnetic structure.

In the case of magnetic structures of the dedicated kind, the table or table plate has a length which is greater that the corresponding dimension of the poles of the magnetic structure and a width which is of the order of the corresponding dimension of the poles.

An embodiment according to the invention allows also a simpler and less expensive patient positioning, due to the fact that the table and the magnetic structure are supported in a way as to be rotated together, the positioning of the patient, by sliding the table relatively to the magnetic structure is carried out in the condition of rotation of the magnet and of the table in which the table is horizontal.

Thus, the means for allowing the sliding displacement of the table as well as the means for driving the displacement of the table can be of reduced strength and of reduced power with respect to the solution disclosed in the above mentioned prior art documents. This on the other hand leads to lower costs, weight reduction and a slighter and simpler construction.

Sliding the table with the patient for positioning the patient relatively to the examining space when the table is horizontal or substantially horizontal means that the effects of the weight of the patient on the sliding movement are reduced to the inertia and to the friction, while the gravitational effects are suppressed.

As it might appear clearly, there is no limitation in the position of the patient relative to the magnetic structure and to the examining space in it.

According to a further improvement, the table might also carry out displacements which are in the transverse direction relative to its longitudinal axis.

Due to the fact that the bed or table is long with respect to the corresponding dimensions of the magnetic structure, the patient may lay down on the table or bed without any difficulty since the table or the bed might be displaced in one of the two opposite end positions in which it extends out from the magnetic structure for a very relevant part.

It is also to be noted that the bed or table can also be designed in a manner as to be used also in other diagnostic devices or apparati.

Providing not only a footrest, but also a seat plate which might be formed by a section of the bed or table allows examinations of the patient also in a sitting position.

In this case there are two options for the patient to enter the magnetic structure. According to a first option the patient enters the magnetic structure with the bed or table in the horizontal position and in lying the patient takes a lying position lying on the bed or table and against the seat. The magnet and the table can be rotated to a substantially vertical position of the bed or table and thus moving the patient to a sitting position. According to a second option, the patient enters the magnetic structure when the bed or table and the magnet are rotated in the vertical position of the bed or table and stands on a footrest or sits down on a seat.

Relating the way of constructing the means for sliding the table and for releasably locking it to the magnetic structure and also the means for rotating table and magnetic structure, the expert in the art is free to choose any kind of known device, such as guides, slides, actuators etc.

One example of a method according to the present invention comprises the following steps:

Providing a magnetic structure having two opposite poles spaced apart one from the other and oriented substantially perpendicularly to a vertical plane and defining a patient imaging space;

Securing a bed or table for the patient to one of the two poles in a slidable way in the longitudinal direction of the bed or table relative to the magnetic structure and between the two poles of the magnetic structure, the bed or table being oriented substantially parallel to the poles, the bed or table preferably having a footrest at one end corresponding to the position of the patient's feet;

Supporting the magnetic structure and the bed or table so that the magnetic structure and the bed or table are rotatable together around an axis which is transverse to the longitudinal axis of the bed or table and parallel to the bed or table;

Rotating the magnetic structure with the table in a patient positioning position in which the bed or table is substantially horizontal;

Sliding the bed or table in one of its extreme end positions, in which the part of the bed or table being outside the magnetic structure is a maximum;

Arranging the patient on the bed or table in a lying position;

Sliding the table or the table along its longitudinal axis relative to the magnetic structure until the magnetic structure is correctly centered with the part of the patient's body to be examined;

Locking the bed or table relative to a further sliding and rotating the magnetic structure together with the bed or table in a position in which the bed or table is not horizontal or perfectly vertical;

Carrying out the imaging procedure;

Rotating the magnetic structure together with the bed or table back in a position in which the bed or table is substantially horizontal;

Sliding the bed or table again in one of the two extreme positions in which the part of the bed or table outside the magnetic structure is a maximum and letting the patient step down from the table.

Alternative to the phases of sliding the bed or table in one of the extreme positions in which the part of the table outside the magnetic structure is a maximum for letting the patient lie down on the plate or step down from the plate, the bed or table may be completely disengaged from the magnetic structure and at the same time engaged in a slidably way onto an independent and separate wheeled supporting frame.

Such an alternative embodiment comprises the steps of:

Providing a magnetic structure having two opposite poles spaced apart one from the other and oriented substantially perpendicularly to a vertical plane and defining a patient imaging space;

Providing a bed or table having at least slides for engaging guides for a longitudinal displacement of the said bed or table;

Providing a bed or table supporting structure which has wheels and which is completely independent from the magnetic structure and/or the imaging apparatus;

Providing one of the poles of the magnetic structure and the bed or table supporting frame with identical guides with which the slides of the bed or table can be engaged;

Rotating the magnetic structure in a position in which the guides for the bed or table are substantially horizontal and aligning the table or bed supporting frame with its guides aligned with the guides on the pole of the magnetic structure;

Providing a bed or table supporting structure with a bed or table arranged on it and letting the patient lie down on the said bed or table;

Sliding the bed or table along its longitudinal direction away from the supporting structure and against the pole having the guides and engaging at the same time the free end of the slides of the bed or table with the guides on the pole;

Sliding the bed or table with the patient on it until the plate is completely disengaged from the supporting frame and engaged with the pole of the magnetic structure;

Sliding further the bed or table along its longitudinal axis relative to the magnetic structure until the magnetic structure is correctly centered with the part of the patient's body to be examined;

Providing the bed or table with a footrest at one end corresponding to the position of the patient's feet.

Supporting the magnetic structure and the bed or table in such a way as to be rotatable together around an axis which is transverse to the longitudinal axis of the bed or table and parallel to the bed or table;

Locking the bed or table relative to a further sliding and rotating the magnetic structure together with the bed or table with the patient on it in a position in which the bed or table is not horizontal or perfectly vertical.

Carrying out the imaging procedure;

Rotating the magnetic structure together with the bed or table back in a position in which the bed or table is substantially horizontal;

Sliding the bed or table back away from the pole of the magnetic structure onto the supporting frame.

According to a further embodiment, the bed or table is transferred onto the pole of the magnetic structure from the supporting frame and back from the pole on the said supporting frame after examination by sliding the bed or table always in the same longitudinal direction of the bed or table, so that a further step of the method includes displacing the supporting frame from the first side of the magnetic structure at which the bed or table has been transferred to the pole to the second opposite side of the pole and aligning the guides of the supporting frame with the guides on the pole of the magnetic structure;

Sliding the bed or table further in the same direction of transfer for transferring the bed or table with the patient on it from the pole again to the supporting frame.

The above mentioned method may provide a rotation of the magnetic structure together with the patient lying on it from the horizontal position to a nonhorizontal position which in intermediate with respect to the horizontal position and to the vertical position.

A further embodiment of imaging may comprise the following steps:

Providing a magnetic structure having two opposite poles spaced apart one from the other and oriented substantially perpendicularly to a vertical plane and defining a patient imaging space;

Securing a bed or table for the patient to one of the two poles in a slidable way in the longitudinal direction of the bed or table relative to the magnetic structure and between the two poles of the magnetic structure, the bed or table being oriented parallel to the poles.

Supporting the magnetic structure and the bed or table in such a way to be rotatable together around an axis which is transverse to the longitudinal axis of the bed or table and parallel to the said bed or table;

Rotating the magnetic structure together with the bed or table in a position in which the bed or table is not horizontal or perfectly vertical;

Providing a seat plate which is secured at an angle to the vertical bed or table;

Letting the patient sit down on the seat plate;

Carrying out the imaging procedure;

Letting the patient step out of the magnetic structure.

According to a further embodiment, each one of the alternative methods may further comprise the step of sliding the bed or table or the seat plate transverse to the longitudinal axis of the bed or table.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. A method for magnetic resonance imaging with a magnetic structure having two opposite poles spaced apart one from the other and oriented substantially perpendicular to a vertical plane and defining a patient imaging space; and a table for a patient secured to one of the two poles in a slidable way in a longitudinal direction of the table relative to the magnetic structure and between the two poles of the magnetic structure, the table being oriented parallel to the poles, the table having a footrest at one end thereof, the magnetic structure and the table being rotatable together around an axis which is transverse to a longitudinal axis of the table and parallel to the table, the method comprising:

rotating the magnetic structure with the table to a patient positioning position in which the table is substantially horizontal;

sliding the table to an end position, in which a part of the table is outside the magnetic structure;

arranging the patient on the table in a lying down position;

sliding the table along its longitudinal axis relative to the magnetic structure until the magnetic structure is correctly centered with a part of the patient's body to be examined;

locking the table relative to the magnetic structure and rotating the magnetic structure together with the table in a position in which the table is not horizontal;

carrying out an imaging procedure;

rotating the magnetic structure together with the table to a position in which the table is substantially horizontal; and sliding the table to a position in which a part of the table is not between the two opposite poles and letting the patient step down from the table.

2. The method of claim 1, wherein the imaging is of the vertebral column.

3. The method according to claim 1, comprising the steps of sliding the table transverse to the longitudinal axis of the table.

4. A method for carrying out magnetic resonance imaging with a magnetic structure having two opposite poles spaced apart one from the other and oriented substantially perpendicular to a vertical plane and defining a patient imaging space; and a table having a footrest at one end and slides for engaging guides for a longitudinal displacement of the table; and a table supporting structure which has wheels and which is completely independent from the magnetic structure, one of the poles of the magnetic structure and the table supporting structure have identical guides with which the slides of the table are adapted to engage, the method comprising:

rotating the magnetic structure such that the guides for the table are horizontal and aligning the guides of the table supporting structure with the guides on the pole of the magnetic structure;

lying the patient down on the table;

sliding the table along a longitudinal direction thereof away from the table supporting frame and toward the pole having the guides and engaging at the same time a free end of the slides of the table with the guides on the pole;

sliding the table with the patient on the table until the table is completely disengaged from the table supporting structure and engaged with the pole of the magnetic structure;

sliding further the table along its longitudinal axis relative to the magnetic structure until the magnetic structure is correctly centered with a part of the patient's body to be examined;

supporting the magnetic structure and the table in such a way as to be rotatable together around an axis which is transverse to the longitudinal axis of the table and substantially parallel to the table;

locking the table relative to further sliding and rotating the magnetic structure together with the table with the patient on it in a position in which the table is not horizontal;

carrying out the imaging procedure;

rotating the magnetic structure together with the table back to a position in which the table is substantially horizontal;

sliding the table away from the pole of the magnetic structure onto the table supporting structure.

5. A method according to claim 4, comprising the further steps of:

displacing the table supporting structure from the first side of the magnetic structure at which the table has been transferred to the pole to a second opposite side of the pole and aligning the guides of the table supporting structure with the guides on the pole of the magnetic structure;

sliding the table further in the same direction of transfer for transferring the table with the patient on it from the pole again to the table supporting structure.

6. The method according to claim 4, wherein the magnetic structure and table are rotated to a position in which the table is not vertical.

7. The method of claim 4, wherein the imaging is of the vertebral column.

8. The method according to claim 4, comprising the steps of sliding the table transverse to the longitudinal axis of the table.

9. A method for carrying out magnetic resonance imaging with a magnetic structure having two opposite poles spaced apart one from the other and oriented substantially perpendicular to a vertical plane and defining a patient imaging space; and a table for a patient to one of the two poles in a slidable way in a longitudinal direction of the table relative to the magnetic structure and between the two poles of the magnetic structure, the table being oriented substantially parallel to the poles; the magnetic structure and the table being rotatable together around an axis which is transverse to the longitudinal axis of the table and parallel to the table, the method comprising:

rotating the magnetic structure together with the table in a position in which the table is not horizontal;

providing a seat plate secured at an angle to the table;

sitting the patient down on the seat plate;

sliding the table transverse to the longitudinal axis of the table;

rotating the magnetic structure together with the table to a position in which the table is not vertical;

carrying out the imaging procedure;

sliding the table to a position in which part of the table is not between the two opposite poles; and letting the patient step out of the magnetic structure.

10. The method of claim 9, wherein the imaging is of the vertebral column.

* * * * *